United States Patent
Berman

(10) Patent No.: US 7,406,153 B2
(45) Date of Patent: Jul. 29, 2008

(54) CONTROL OF X-RAY BEAM SPOT SIZE

(75) Inventor: David Berman, Kiryat Tivon (IL)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 56 days.

(21) Appl. No.: 11/503,979

(22) Filed: Aug. 15, 2006

(65) Prior Publication Data
US 2008/0043911 A1    Feb. 21, 2008

(51) Int. Cl.
*G01N 23/201* (2006.01)
(52) U.S. Cl. .......................................... 378/86; 378/89
(58) Field of Classification Search .............. 378/70–90
See application file for complete search history.

(56) References Cited
U.S. PATENT DOCUMENTS

| | | | |
|---|---|---|---|
| 4,725,963 A | 2/1988 | Taylor et al. ................... | 378/20 |
| 4,989,226 A | 1/1991 | Woodbury et al. ........... | 378/145 |
| 5,151,588 A | 9/1992 | Kiri et al. ................ | 250/208.1 |
| 5,574,284 A | 11/1996 | Farr ..................... | 250/370.06 |
| 5,619,548 A | 4/1997 | Koppel ......................... | 378/70 |
| 5,740,226 A | 4/1998 | Komiya et al. ................ | 378/70 |
| 5,923,720 A | 7/1999 | Barton et al. ................ | 378/84 |
| 5,949,847 A | 9/1999 | Terada et al. ................ | 378/90 |
| 6,041,098 A | 3/2000 | Touryanski et al. ........... | 378/70 |
| 6,192,103 B1 | 2/2001 | Wormington et al. ......... | 378/73 |
| 6,226,347 B1 | 5/2001 | Golenhofen ................. | 378/45 |
| 6,226,349 B1 | 5/2001 | Schuster et al. .............. | 378/84 |
| 6,381,303 B1 | 4/2002 | Vu et al. ....................... | 378/46 |
| 6,389,102 B2 | 5/2002 | Mazor et al. .................. | 378/89 |
| 6,453,006 B1 | 9/2002 | Koppel et al. ................. | 378/86 |
| 6,507,634 B1 | 1/2003 | Koppel et al. ................. | 378/54 |
| 6,512,814 B2 | 1/2003 | Yokhin et al. ................. | 378/82 |
| 6,556,652 B1 | 4/2003 | Mazor et al. .................. | 378/86 |
| 6,625,250 B2 * | 9/2003 | Houge ......................... | 378/84 |
| 6,639,968 B2 | 10/2003 | Yokhin et al. ................. | 378/70 |
| 6,643,354 B2 | 11/2003 | Koppel et al. ................. | 378/86 |

(Continued)

FOREIGN PATENT DOCUMENTS

JP    09308339    12/1997

OTHER PUBLICATIONS

Jones, et al., "Small angle x-ray scattering for sub-100 nm pattern characterization", Applied Physics Letters 83:19 (2003), pp. 4059-4061.

(Continued)

*Primary Examiner*—Jurie Yun
(74) *Attorney, Agent, or Firm*—Smith, Gambrell & Russell, LLP

(57) ABSTRACT

Apparatus for analysis of a sample includes a radiation source, which is configured to direct a beam of radiation along a beam axis to impinge on a target area on a surface of the sample. A detector assembly is configured to sense the radiation scattered from the sample. A beam control assembly includes a beam blocker, which has a lower side adjoining the surface of the sample, and which contains front and rear slits perpendicular to the lower side that together define a beam plane that contains the beam axis and passes through the target area. The front slit is located between the radiation source and the target area, and the rear slit is located between the target area and the detector assembly.

26 Claims, 6 Drawing Sheets

U.S. PATENT DOCUMENTS

| | | | |
|---|---|---|---|
| 6,680,996 B2 | 1/2004 | Yokhin et al. | 378/70 |
| 6,711,232 B1 | 3/2004 | Janik | 378/70 |
| 6,744,950 B2 | 6/2004 | Aleksoff | 385/48 |
| 6,750,952 B2 | 6/2004 | Grodnensky et al. | 355/77 |
| 6,771,735 B2 | 8/2004 | Janik et al. | 378/70 |
| 6,813,338 B2 | 11/2004 | Takata et al. | 378/75 |
| 6,895,075 B2 | 5/2005 | Yokhin et al. | 378/90 |
| 7,242,743 B2 * | 7/2007 | Fewster | 378/71 |
| 2001/0028699 A1 | 10/2001 | Iwasaki | 378/84 |
| 2001/0043668 A1 | 11/2001 | Hayashi et al. | 378/89 |
| 2002/0097837 A1 | 7/2002 | Fanton et al. | 378/82 |
| 2002/0110218 A1 | 8/2002 | Koppel et al. | 378/86 |
| 2003/0157559 A1 | 8/2003 | Omote et al. | 435/7.1 |
| 2004/0052330 A1 | 3/2004 | Koppel et al. | 378/46 |
| 2004/0156474 A1 | 8/2004 | Yokhin et al. | 378/70 |
| 2004/0218717 A1 | 11/2004 | Koppel et al. | 378/70 |
| 2006/0062351 A1 | 3/2006 | Yokhin et al. | 378/86 |

OTHER PUBLICATIONS

Stommer, "X-ray scattering from silicon surfaces", in Semiconductor International (May 1, 1998).

Yoneda, "Anomalous surface reflection of X Rays", Physical Review 131, pp. 2010-2013, 1963.

Stommer, et al., "Characterization of semiconductor materials by X-ray scattering", Electrochemical Society Proceedings vol. 99-16, pp. 117-133, 1999.

Bowen, et al., "X-Ray metrology by diffraction and reflectivity", Characterization and Metrology for ULSI Technology, 2000 International Conference (American Institute of Physics, 2001).

Ulyanekov, "Introduction to high resolution X-Ray diffraction", Workshop on X-ray characterization of thin layers (Uckley, May 21-23, 2003).

Naudon, et al., "New apparatus for grazing X-ray reflectometry in the angle-resoived dispresive mode", J. Appl. Cryst. 1989, vol. 22, pp. 46-464.

F. Neissendorfer, et al., "The Energy-dispersive reflectometer/diffractometer at BESSY-I", Meas. Sci. Technol. 10(1999) 354-361.

A.R. Powell, et al., "X-ray diffraction and reflectivity characterization of SiGe superlattice structures", Semicond. Sci. Technol. 7(1992), 627-631.

* cited by examiner

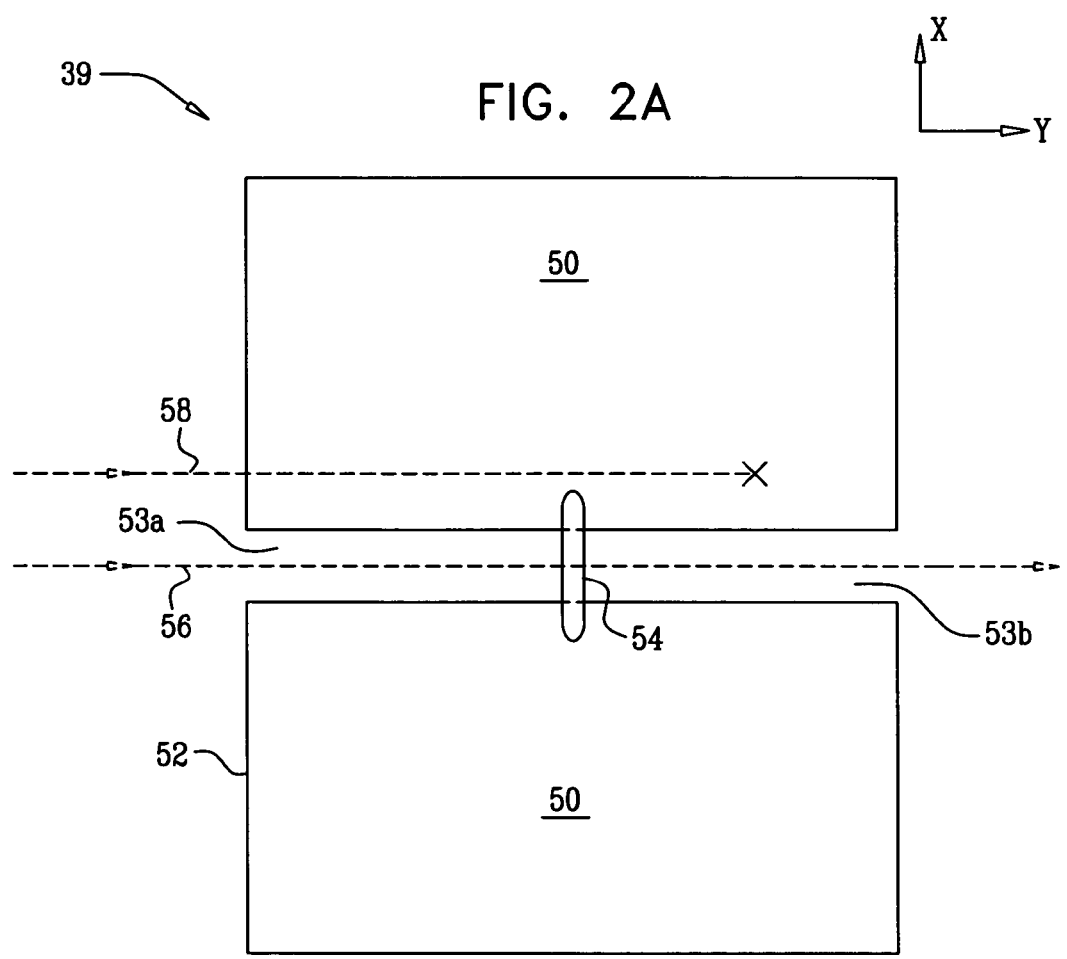

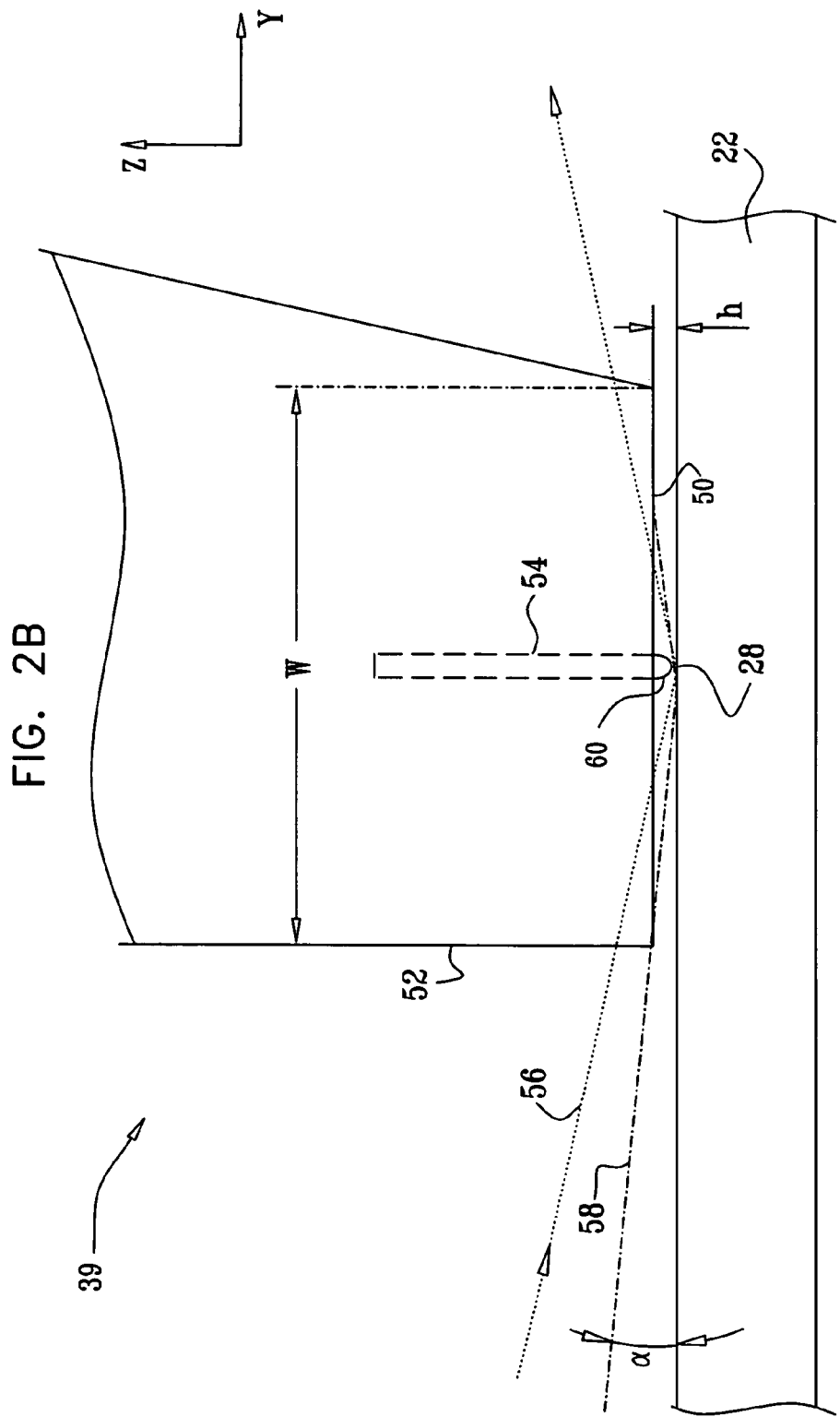

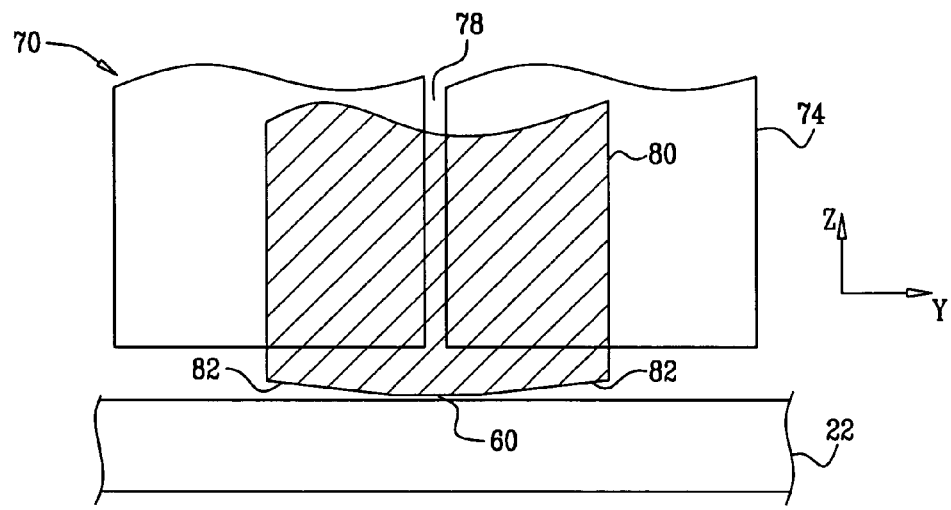
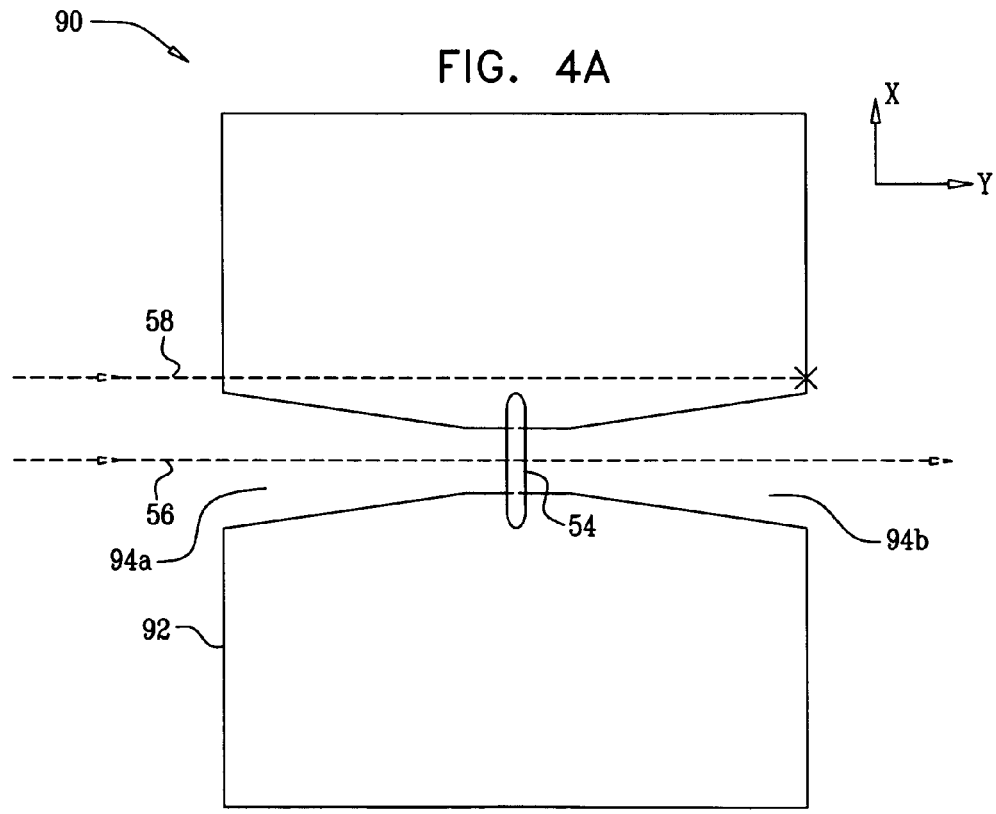

CONTROL OF X-RAY BEAM SPOT SIZE

FIELD OF THE INVENTION

The present invention relates generally to analytical instruments, and specifically to instruments and methods for material analysis using X-rays.

BACKGROUND OF THE INVENTION

X-ray reflectometry (XRR) is a well-known technique for measuring the thickness, density and surface quality of thin film layers deposited on a substrate. X-ray reflectometers typically operate by irradiating a sample with a beam of X-rays at grazing incidence, i.e., at a small angle relative to the surface of the sample, in the vicinity of the total external reflection angle of the sample material. An X-ray detector, which may comprise a detector array, senses the reflected X-rays. Measurement of X-ray intensity reflected from the sample as a function of angle gives a pattern of interference fringes, which is analyzed to determine the properties of the film layers responsible for creating the fringe pattern. Exemplary systems and methods for XRR are described in U.S. Pat. Nos. 5,619,548, 5,923,720, 6,512,814, 6,639,968, and 6,771,735, whose disclosures are incorporated herein by reference.

The spot size and angular extent of the X-ray beam that is incident on the sample surface affect the spatial and angular resolution of XRR measurement results. In order to control these factors, U.S. Pat. No. 6,639,968, for example, provides a dynamic knife edge and shutter interposed in the X-ray beam. For measurements at low incidence angles, the knife edge is lowered very near to the surface, intercepting the incident X-ray beam and thus shortening the lateral dimension of the spot on the surface. (In the context of the present patent application and in the claims, the dimension of the spot in the direction along the surface that is parallel to the projection of the beam axis on the surface is referred to in the conventional manner as the lateral dimension, while the dimension in the direction perpendicular to the beam axis is referred to as the transverse dimension.) For high-angle measurements, at which the dynamic shutter is used, the knife edge may be raised out of the way, to allow the full intensity of the X-ray beam to be used. As another example, U.S. Pat. No. 6,771,735 uses two "gates" for blocking certain parts of the X-ray beam.

U.S. Pat. No. 6,895,075, whose disclosure is incorporated herein by reference, describes a system that combines XRR with small-angle X-ray scattering measurement (SAXS). The system uses the dynamic knife edge and shutter of U.S. Pat. No. 6,639,968 for controlling the incident beam in the vertical direction (perpendicular to the surface of the sample), together with a slit for limiting the transverse dimension of the beam in the horizontal direction. The minimum slit width is said to be about 100 μm.

U.S. Patent Application Publication 2006/0062351, whose disclosure is incorporated herein by reference, describes another multifunction X-ray analysis system, which combines XRR with SAXS and X-ray diffraction (XRD) measurement. In one embodiment, shown in FIG. 5 of this publication, a knife edge is made of a cylindrical, X-ray absorbing material, such as a metal wire. This arrangement is said to permit the lower edge of the knife to be placed very close to the surface of the sample, on the order of 3 μm above the surface, without risk of damaging the sample. The wire can be aligned with the surface accurately and thus provides a small gap above the surface whose effective height is uniform over the entire angular range of interest, typically 0-4°.

Based on this example, it will be understood that in the context of the present patent application and in the claims, the term "knife edge" refers to any type of straight edge (not necessarily very sharp) that is positioned near the surface of a sample in order to create this a gap between the knife edge and the surface and to block X-rays outside the gap.

SUMMARY OF THE INVENTION

Embodiments of the present invention provide improved apparatus and methods for controlling the effective spot size and angular extent of a beam of radiation on a target area on the surface of a sample. The term "effective spot size," as used herein, refers to the size of the spot on the surface of the sample from which scattered radiation (reflected or otherwise) is received by a detector.

In these embodiments, a beam control assembly comprises a beam blocker, having a lower side that may be positioned in close proximity to the surface of the sample. The beam blocker contains front and rear slits, which are typically perpendicular to the lower side of the beam blocker. The beam blocker is positioned so that the slits are located on opposites sides of the target area and define a beam plane that contains the target area. In some embodiments, a beam limiter is positioned within the beam plain so as to block a portion of the plain. The beam limiter has a knife edge, which is transverse to the beam plane and typically protrudes below the lower side of the beam blocker. The beam control assembly may be used in various X-ray inspection techniques, such as XRR, XRD, and SAXS, as defined above.

In a typical XRR scenario, for example, the assembly is positioned so that the beam plane is aligned with an X-ray beam that is incident on the sample, and so that the knife edge is located adjacent to the target area and parallel to, but not touching, the surface of the sample. In this configuration, the transverse dimension of the X-ray spot formed on the surface and the transverse angular spread of the beam are limited by the width of the slits. The lateral dimension of the spot is limited by the knife edge. (Alternatively, the beam blocker may be used by itself to limit the transverse dimension of the spot, without the knife edge and/or with other means for limiting the lateral spot dimension.) The spot size may thus be made very small, on the order of a few microns or less in the transverse direction. Furthermore, the beam blocker may be made wide enough, and the lower side of the beam blocker may be placed close enough to the sample surface so that all X-rays that are incident on the sample surface outside the area of the slits at angles above some minimum angle strike the beam blocker and are thus prevented from reaching the XRR detector. (X-rays below this minimum angle may be blocked separately by a dynamic shutter, as described in the Background of the Invention.) Use of the beam control assembly thus facilitates X-ray analysis of the sample surface with much finer spatial and angular resolution than could otherwise be achieved.

There is therefore provided, in accordance with an embodiment of the present invention, apparatus for analysis of a sample, including:

a radiation source, which is configured to direct a beam of radiation along a beam axis to impinge on a target area on a surface of the sample;

a detector assembly, which is configured to sense the radiation scattered from the sample; and a beam control assembly, including a beam blocker, which has a lower side adjoining the surface of the sample, and which contains front and rear slits perpendicular to the lower side that together define a beam plane that contains the beam axis and passes through the target area, wherein the front slit is located between the radiation source and the target area, and the rear slit is located between the target area and the detector assembly.

In a disclosed embodiment, the radiation source is configured to generate the beam so that the radiation converges on the target area over a range of elevation angles relative to the surface of the sample, and the detector assembly is configured to resolve the scattered radiation as a function of elevation angle. Typically, the radiation includes X-rays, and the detector assembly is configured to detect a reflectometric spectrum of the X-rays, which is indicative of a characteristic of a thin film on the surface of the sample in the target area.

Typically, the beam blocker has a width between the front and rear slits and is positioned so that the lower side is separated from the surface of the sample by a gap of a given height, and the width and height are chosen so as to block the radiation that is emitted from the radiation source at elevation angles greater than a given angle relative to the surface of the sample from passing through the gap and impinging on the detector assembly. In one embodiment, the width and height are chosen so as to satisfy a relation $\alpha_{min} \cong 2 h/W$, wherein $\alpha_{min}$ is the given angle, h is the height, and W is the width. Additionally or alternatively, the apparatus includes a shutter, which is located between the radiation source and the sample and is positioned so as to block the radiation that is emitted from the radiation source below the given angle.

In some embodiments, the beam control assembly includes a beam limiter, which is positioned between the front and rear slits transverse to the beam plane, and which includes a knife edge, which protrudes between the lower side of the beam blocker and the sample adjacent and parallel to the surface of the sample in target area so as to define a gap between the surface of the sample and the knife edge and to block a portion of the beam that does not pass through the gap. In one embodiment, a lower side of the knife edge, adjacent to the target area, is rounded, and the gap is no greater than 3 μm. Additionally or alternatively, the beam limiter includes a central portion, which intercepts the beam plane and includes the knife edge, and includes outer edges, which are adjacent to the surface of the sample outside the central portion and angle upward away from the knife edge.

In one embodiment, the beam blocker includes a unitary block of material having a longitudinal slit formed therethrough, the longitudinal slit including the front and rear slits. In another embodiment, the beam blocker includes separate front and rear blocker units, which respectively contain the front and rear slits. In yet another embodiment, at least one of the front and rear slits has a profile of non-uniform width in a direction transverse to the beam plane.

In a disclosed embodiment, the front and rear slits have a dimension transverse to the beam axis that is no greater than 50 μm, and may be no greater than 10 μm.

There is also provided, in accordance with an embodiment of the present invention, a method for analysis of a sample, including:

directing a beam of radiation along a beam axis to impinge on a target area on a surface of the sample;

interposing in the beam a beam blocker containing front and rear slits that together define a beam plane that contains the beam axis and passes through the target area, so that a lower side of the beam blocker adjoins the surface of the sample and so that the beam of radiation passes through the front slit before impinging on the target area, and the radiation scattered from the sample within the beam plane passes through the rear slit; and sensing the radiation scattered from the sample after passage of the radiation through the rear slit.

There is additionally provided, in accordance with an embodiment of the present invention, apparatus for analysis of a sample, including:

a radiation source, which is configured to direct a beam of radiation along a beam axis to impinge on a target area on a surface of the sample;

a detector assembly, which is configured to sense the radiation scattered from the sample; and a beam control assembly, which is interposed between the radiation source and the sample as to restrict the beam that impinges on the sample to a dimension in a direction transverse to the beam axis that is no greater than 50 μm.

In some embodiments, the dimension is no greater than 10 μm.

There is further provided, in accordance with an embodiment of the present invention, a method for analysis of a sample, including:

directing a beam of radiation along a beam axis to impinge on a target area on a surface of the sample;

applying a beam control assembly so as to restrict the beam that impinges on the sample to a dimension in a direction transverse to the beam axis that is no greater than 50 μm; and sensing the radiation scattered from the sample.

The present invention will be more fully understood from the following detailed description of the embodiments thereof, taken together with the drawings in which:

BRIEF DESCRIPTION OF THE DRAWINGS

FIGS. 2A and 2B are schematic bottom and side views, respectively, of a beam control assembly, in accordance with an embodiment of the present invention;

FIGS. 3B and 3C are schematic sectional views of the beam control assembly of FIG. 3A, taken along lines IIIB-IIIB and IIIC-IIIC in FIG. 3A, respectively; and FIGS. 4A and 4B are schematic bottom and side views, respectively, of a beam control assembly, in accordance with yet another embodiment of the present invention.

DETAILED DESCRIPTION OF EMBODIMENTS

Figure 1:
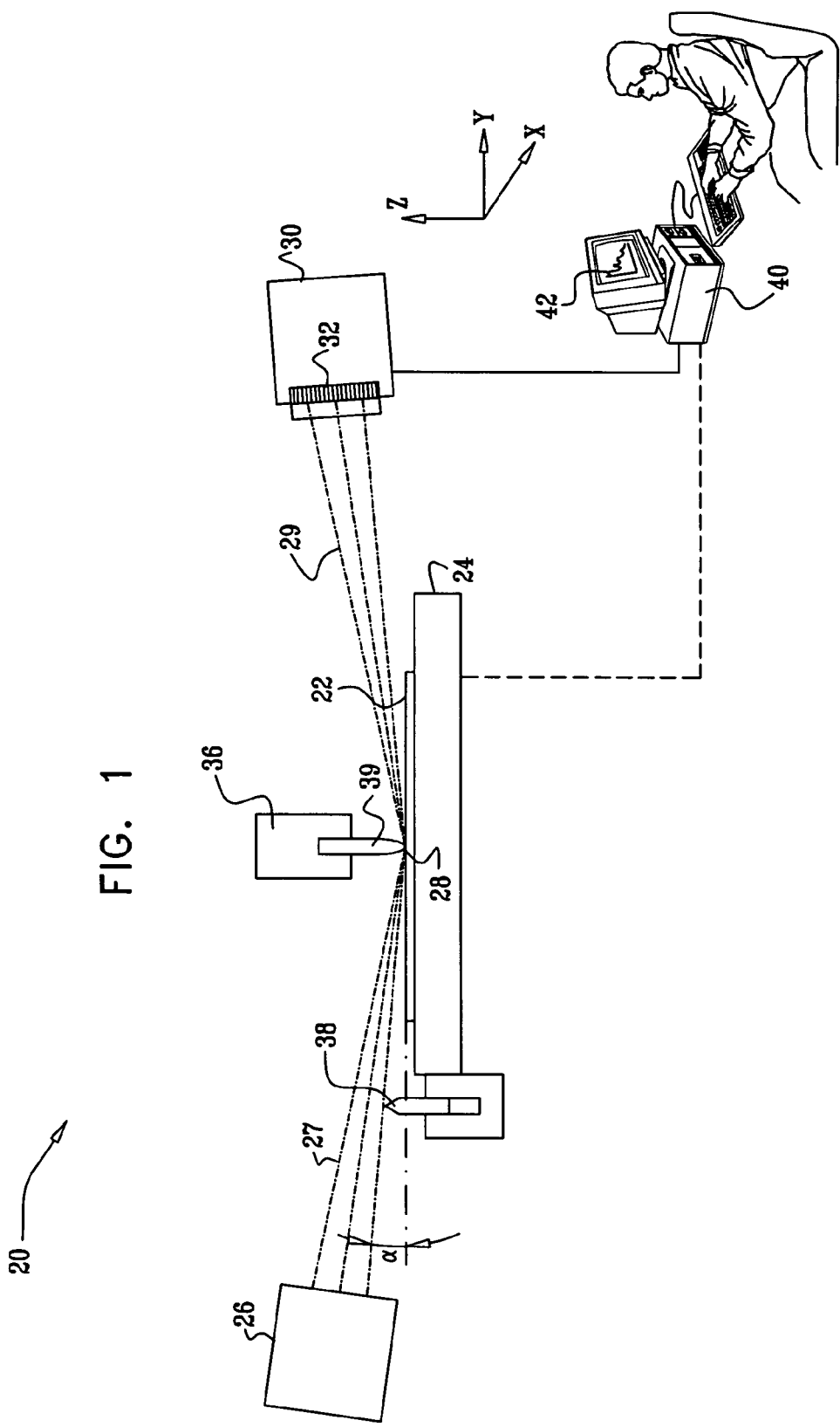
FIG. 1 is a schematic, side view of a system for XRR, in accordance with an embodiment of the present invention.

FIG. 1 is a schematic illustration of a system 20 for X-ray reflectometry (XRR) of a sample, such as a semiconductor wafer 22, in accordance with an embodiment of the present invention. System 20 can be used, for example, in a semiconductor fabrication facility, for identifying process faults and estimating process parameters at different stages of the wafer production process. Sample 22 is mounted on a mounting assembly, such as a motion stage 24, allowing accurate adjustment of the position and orientation of the sample. An X-ray source 26 irradiates a target area 28 on sample 22 with a converging beam 27 of X-rays. X-rays in a diverging beam 29 that is scattered from the sample are collected by a detector assembly 30, which typically comprises a detector array 32. Details of X-ray sources and detector assemblies that may be used in this configuration are described in the publications cited in the Background of the Invention.

For XRR measurement, converging beam 27 strikes area 28 at a grazing angle, typically over a range of incident angles from about 0° to 4.5°, although larger or smaller ranges may be used. In this configuration, detector assembly 30 collects diverging beam 29 over a range of angles in the vertical direction, as a function of elevation angle ($\phi$) between about 0° and at least 2°, and typically up to 3°. This range includes angles both below and above the critical angle of the sample for total external reflection, $\Phi_c$. (For clarity of illustration, the angular ranges shown in the figures are exaggerated, as is the elevation of source 26 and detector assembly 30 above the plane of sample 22. For convenience and clarity in this figure and in the description that follows, the sample plane is arbitrarily taken to be the X-Y plane, wherein the Y-axis is parallel to the projection of the axis of the X-ray beam on the sample surface. The Z-axis is in the vertical direction, perpendicular to the sample plane.)

A dynamic beam control assembly 36 and shutter assembly 38 are used to limit the angular extent of incident beam 27 of the X-rays in the vertical (Z) and horizontal (X) directions. The beam control assembly comprises a knife edge unit 39, which is described in detail with reference to the figures that follow. The heights of the knife edge unit and shutter relative to the sample surface are adjustable depending on the type of measurement being made and the range of measurement angles of interest.

A signal processor 40 receives and analyzes the output of detector assembly 30, so as to determine a distribution 42 of the flux of X-ray photons scattered from sample 22 as a function of angle at a given energy or over a range of energies. Typically, sample 22 has one or more thin surface layers, such as thin films, at area 28, and distribution 42 as a function of angle exhibits a structure that is characteristic of interference effects due to the outer layer and interfaces between the layers. Processor 40 analyzes characteristics of the angular distribution in order to determine characteristics of one or more of the surface layers of the sample, and may also serve as a system controller, to set and adjust the positions and configurations of the other system components.

In some XRR applications, such as testing of thin film layers on patterned semiconductor wafers, it is desirable to make the spot size of the X-ray beam in target area 28 very small, on the order of about 1-10 μm, at least in the transverse (X) dimension. With a focal spot this small, together with appropriate positioning of motion stage 24, the target area of the incident X-ray beam can be made to overlap a homogeneous area of the wafer, such as a scribe line between dies, aligned along the Y-axis. "Homogeneous" in this sense means that the surface layer and each of the underlying thin film layers of the wafer are uniform over the area of the focal spot. Under these conditions, the angular resolution of distribution 42 is enhanced, since the blurring effect of non-uniformities is reduced. The spatial resolution on the sample surface is, of course, increased, as well. These enhancements are achieved by means of the novel design of beam control assembly 36, as described hereinbelow.

FIGS. 2A and 2B schematically show details of knife edge unit 39, in accordance with an embodiment of the present invention. FIG. 2A is a bottom view (as seen from the surface of wafer 22), while FIG. 2B is a side view. Unit 39 comprises a beam blocker 52, having a longitudinal slit 53 in which a beam limiter 54 is fitted. The beam limiter thus divides slit 53 into a front slit 53a and a rear slit 53b, which are referred to collectively simply as slit 53. The beam blocker and beam limiter are both made of metal or other X-ray absorbing materials. For example, the beam blocker and beam limiter may be made of tungsten-carbon with nickel additive.

Typically, the position (and particularly the height) of the beam limiter is adjustable relative to the beam blocker. Alternatively, although the beam blocker and beam limiter are shown and described, for the sake of clarity, as separate units, they may alternatively be integrally manufactured from a single piece of material. Further alternatively or additionally, although beam blocker 52 is shown in the figures as comprising solid, unitary blocks of material, other modes of construction may be used to achieve the structural and functional features that are described herein and recited in the claims. Exemplary alternative embodiments are described hereinbelow with reference to FIGS. 3A-3C and FIGS. 4A and 4B.

Beam blocker 52 has a lower side 50 that defines a plane, which is positioned in proximity to and a short distance above the surface of wafer 22. Although the lower side is shown in the figures as comprising a flat, unitary surface, parallel to the wafer surface, it may alternatively have recesses or other surface variations. In some embodiments, the lower side of the beam blocker may define a "virtual surface," i.e., a plane in space that is defined by the features of the beam blocker that are in proximity to the wafer surface. The alternative embodiments of FIGS. 3A-3C and FIGS. 4A and 4B have this sort of lower sides.

The distance between lower side 50 and the surface of wafer 22, marked h in FIG. 2B, may be on the order of about 10 μm, although larger or smaller distances may be used depending on application requirements. The width of beam blocker 52 in the axial (Y) direction, labeled W in FIG. 2B, is typically much greater than h. Slit 53 defines a beam plane, which is aligned with the incident X-ray beam in the Y-Z plane and thus passes through target area 28. The slit is typically on the order of 50 μm wide, but may be made as narrow as desired (and technically feasible) in order to limit the spread of the beam in the transverse (X) direction. For example, the transverse dimension of the slit may be 10 μm or less in order to limit the transverse dimension of the X-ray spot on sample 22 accordingly. Beam blocker 52 is positioned so that front slit 53a is located between source 26 and target area 28, while rear slit 53b is located between the target area and detector array 32. Thus, X-rays in the Y-Z plane within the slit, such as a ray 56, may pass through slit 53a over a range of elevation angles, reflect from the surface of wafer 22 beneath beam limiter 54, and exit from slit 53b to impinge on detector array 32.

X-rays outside slit 53 are either blocked by the front side of beam blocker 52, or penetrate the gap between the lower side of the beam blocker and the surface of the wafer. Those of the latter rays that strike the wafer surface at an elevation angle greater than a certain minimum angle $\alpha_{min}$, such as a ray 58, will reflect from the wafer and then impinge on the lower side of beam blocker 52, where they are absorbed. For a given W and h, it can be seen that $\alpha_{min} \cong 2h/W$. Rays incident at angles below $\alpha_{min}$ may be blocked by appropriate setting of shutter 38. In a typical XRR configuration, $\alpha_{min}$ may be set slightly below the critical angle $\Phi_c$ of wafer 22, i.e., $\alpha_{min}=0.2°$. Under these conditions, with h=10 μm, a beam blocker of width $W \geq 5.73$ mm will block substantially all rays above $\alpha_{min}$.

Alternatively, $\alpha_{min}$ may be varied depending on application requirements. For example, blocker 52 may be positioned higher above wafer 22, where it will not affect measurements made at low angles. Since XRR signals from the surface layer tend to be strong in any case at such low angles, any background effects that may be mixed into the signal from areas outside the desired measurement area (such as areas off the scribe line, when measurements are made along the scribe line) tend to be insignificant. Slit 53 will still limit the beam at higher angles, where background effects may be more problematic.

Beam limiter 54 is held by unit 39 in a plane transverse to slit 53, blocking at least the lower portion of the slit. The beam limiter has a knife edge 60 that typically protrudes below the lower side of beam blocker 52. Alternatively, in some applications, the beam limiter may be withdrawn so that the knife edge is above the lower side of the beam blocker. To minimize the lateral (Y) dimension of the X-ray spot on the surface of wafer 22, knife edge 60 may be positioned very close to the wafer surface, in the range of 1-3 µm from the surface, for example. In order to reduce the possibility of damage to the wafer and maintain an effective height of the knife edge over the wafer that is uniform over the entire angular range of interest (such as 0-4°), edge 60 may be rounded, as described in the above-mentioned U.S. Patent Application Publication 2006/0062351. For example, edge 60 may comprise a piece of tantalum wire of suitable diameter. Alternatively, edge 60 may be made by any other suitable process, may comprise any other suitable material (such as the tungsten/carbon/nickel material mentioned above), and may have any other suitable shape that is known in the art.

Figure 3A:
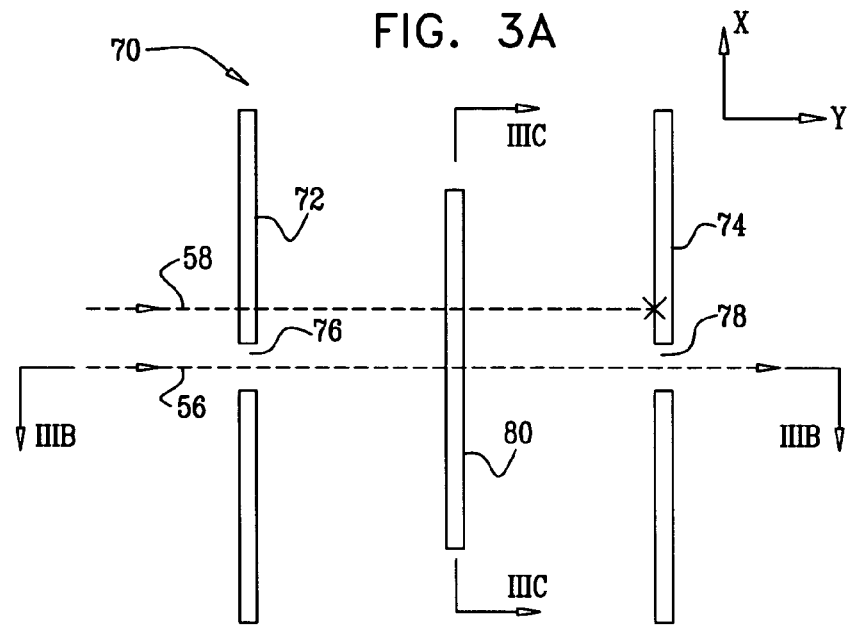
FIG. 3A is a schematic bottom view of a beam control assembly, in accordance with another embodiment of the present invention.
Figure 3B:
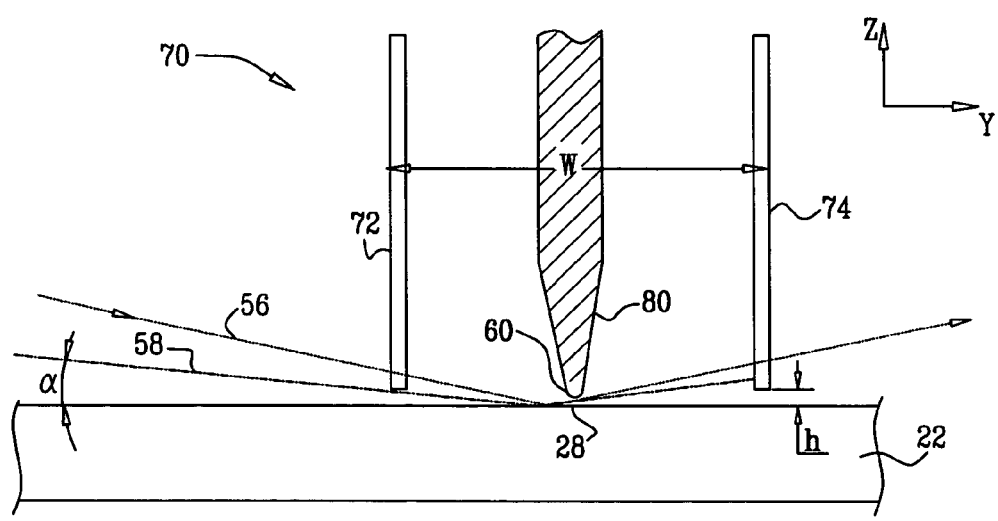

Reference is now made to FIGS. 3A-3C, which schematically illustrate a beam control assembly 70, in accordance with another embodiment of the present invention. Assembly 70 may be used in place of beam control assembly 39 in the system of FIG. 1. FIG. 3A is a bottom view (looking upward along the Z-axis from wafer 22) of assembly 70, while FIGS. 3B and 3C are sectional views, taken along lines IIIB-IIIB and IIIC-IIIC, respectively in FIG. 3A.

The principles of operation of assembly 70 are similar to those of assembly 39, and like elements are marked with the same numbers in the various figures. In assembly 70, however, front and rear blocker units 72 and 74 take the place of beam blocker 52. The blocker units have respective front and rear slits 76 and 78, which fulfill the role of slits 53a and 53b. Typically, blocker units 72 and 74 are aligned and held together in a mount, which moves the units up and down in relation to wafer 22. The lower edges of the two blocker units make the lower side of the beam blocker in this case, and define a surface that is positioned at the height h above the wafer. Alternatively, the two blocker units may be individually adjustable.

A beam limiter 80 is positioned between blocker units 72 and 74 transverse to the plane of slits 76 and 78 and blocking at least part of the radiation in this plane. Typically, edge 60 of the beam limiter is positioned in close proximity to the surface of wafer 22, below the lower surface defined by the lower edges of the blocker units. Alternatively, beam limiter 80 may be withdrawn to a higher position.

As shown in FIG. 3C, beam limiter 80 may be considerably wider than slits 76 and 78. This sort of wide beam limiter is helpful in reducing the amount of stray radiation that may scatter beneath the beam blocker units and strike detector array 32. On the other hand, the wide beam limiter may create difficulties in positioning edge 60 parallel and very close to the wafer surface, particularly since the wafer surface may not be perfectly flat. To ameliorate such difficulties, edge 60 may be formed only in the central part of beam limiter 80, while outer edges 82 angle slightly upward, as shown in the figure. Although for the sake of visual clarity, outer edges 82 are angled sharply relative to edge 60 in FIG. 3C, in practice the outer edges may angle up by much smaller angles, on the order of 0.1° to 1°.

Figure 4B:
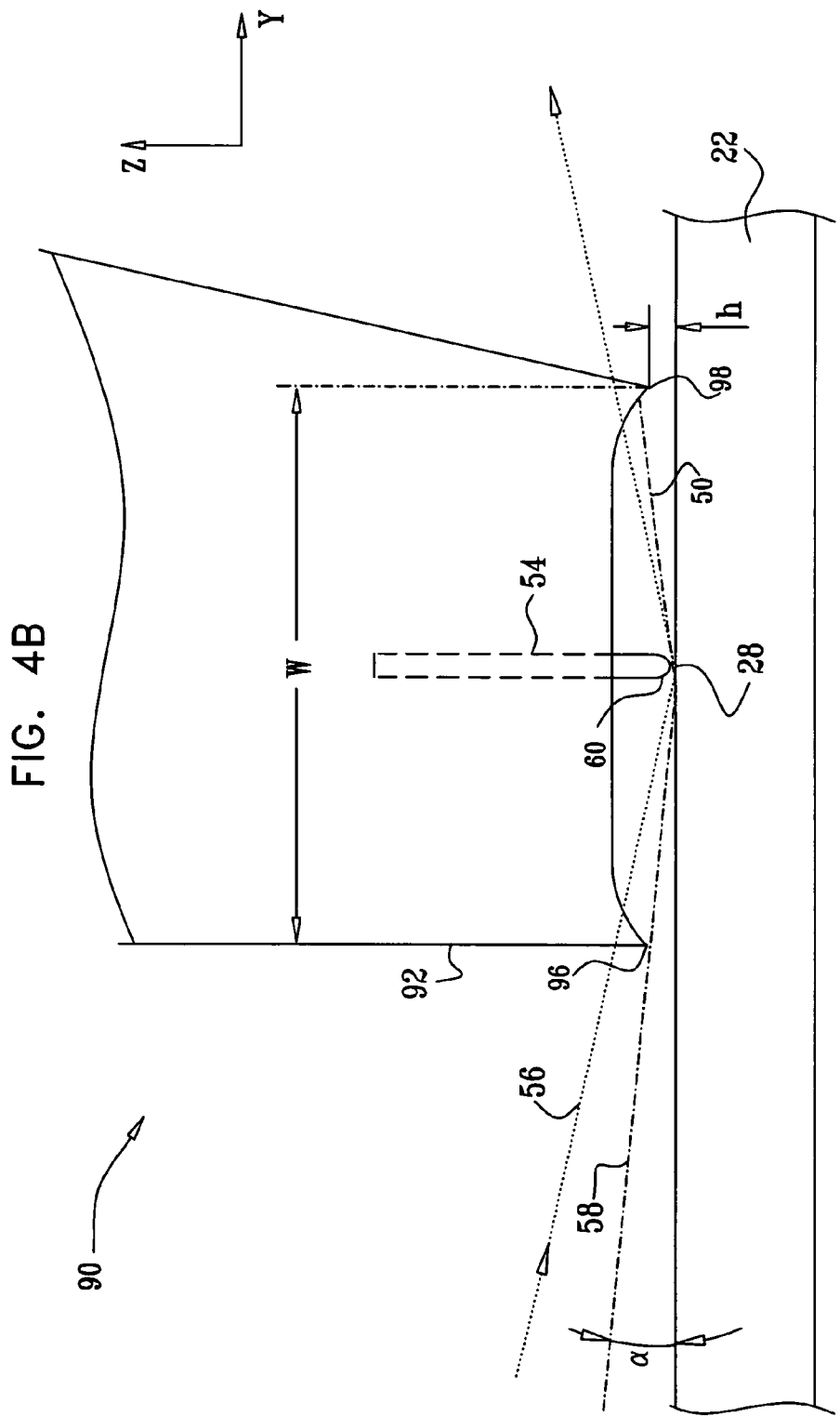

FIGS. 4A and 4B schematically illustrate a beam control assembly 90, in accordance with yet another embodiment of the present invention. Assembly 90 may be used in place of assembly 39 in the system of FIG. 1, and like features are again identified by the same numbers. FIG. 4A is a bottom view of assembly 90, while FIG. 4B is a side view.

Assembly 90 comprises a beam blocker 92 having a slit 94 passing therethrough. As in beam blocker 39, slit 94 is divided into front and rear slits 94a and 94b by beam limiter 54. Slits 94a and 94b have profiles of non-uniform width in the X-direction, as shown in FIG. 4A, with relatively wide outer ends at the front and rear surfaces of the beam blocker, and a narrow waist in the center. In this example, the slit profiles are triangular, although other non-uniform profiles may similarly be used. Since converging beam 27 may converge in the X-direction (together with the Z-direction convergence shown in FIG. 1), the triangular slits can be useful in increasing the amount of beam power that is incident on target area 28 and is reflected onto detector array 32.

As shown in FIG. 4B, the lower side of beam blocker 92 is not flat, but is rather recessed for convenience of alignment with the surface of wafer 22. The lower surface, at height h above the wafer surface, is in this case defined by front and rear lower edges 96 and 98. The shape of beam blocker 92 (as well as the shapes of the other beam blockers and beam limiters shown above) is presented solely by way of example, and alternative shapes that may be used to similar effect will be apparent to those skilled in the art and are considered to be within the scope of the present invention.

Although features of system 20 are described hereinabove with specific reference to XRR, the principles of the present invention, and particularly of the beam control assemblies shown above, may similarly be applied in other areas of X-ray analysis, such as SAXS and XRD. Furthermore, these principles are not limited to the X-ray field, but rather may be applied in analysis using electromagnetic radiation in other ranges of wavelength, such as gamma radiation, as well as particle beam irradiation, that impinges on a sample at an angle. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for analysis of a sample, comprising:
   a radiation source, which is configured to direct a beam of radiation along a beam axis to impinge on a target area on a surface of the sample;
   a detector assembly, which is configured to sense the radiation scattered from the sample; and
   a beam control assembly, comprising a beam blocker, which has a lower side adjoining the surface of the sample, and which contains front and rear slits perpendicular to the lower side that together define a beam plane that contains the beam axis and passes through the target area, wherein the front slit is located between the radiation source and the target area, and the rear slit is located between the target area and the detector assembly.

2. The apparatus according to claim 1, wherein the radiation source is configured to generate the beam so that the radiation converges on the target area over a range of elevation angles relative to the surface of the sample, and wherein the detector assembly is configured to resolve the scattered radiation as a function of elevation angle.

3. The apparatus according to claim 2, wherein the radiation comprises X-rays, and wherein the detector assembly is configured to detect a reflectometric spectrum of the X-rays, which is indicative of a characteristic of a thin film on the surface of the sample in the target area.

4. The apparatus according to claim 1, wherein the beam blocker has a width between the front and rear slits and is positioned so that the lower side is separated from the surface of the sample by a gap of a given height, and wherein the width and height are chosen so as to block the radiation that is emitted from the radiation source at elevation angles greater than a given angle relative to the surface of the sample from passing through the gap and impinging on the detector assembly.

5. The apparatus according to claim 4, wherein the width and height are chosen so as to satisfy a relation $\alpha_{min} \cong 2\,h/W$, wherein $\alpha_{min}$ is the given angle, h is the height, and W is the width.

6. The apparatus according to claim 4, and comprising a shutter, which is located between the radiation source and the sample and is positioned so as to block the radiation that is emitted from the radiation source below the given angle.

7. The apparatus according to claim 1, wherein the beam control assembly comprises a beam limiter, which is positioned between the front and rear slits transverse to the beam plane, and which comprises a knife edge, which protrudes between the lower side of the beam blocker and the sample adjacent and parallel to the surface of the sample in target area so as to define a gap between the surface of the sample and the knife edge and to block a portion of the beam that does not pass through the gap.

8. The apparatus according to claim 7, wherein a lower side of the knife edge, adjacent to the target area, is rounded.

9. The apparatus according to claim 7, wherein the gap is no greater than 3 μm.

10. The apparatus according to claim 7, wherein the beam limiter comprises a central portion, which intercepts the beam plane and comprises the knife edge, and comprises outer edges, which are adjacent to the surface of the sample outside the central portion and angle upward away from the knife edge.

11. The apparatus according to claim 1, wherein the beam blocker comprises a unitary block of material having a longitudinal slit formed therethrough, the longitudinal slit comprising the front and rear slits.

12. The apparatus according to claim 1, wherein the beam blocker comprises separate front and rear blocker units, which respectively contain the front and rear slits.

13. The apparatus according to claim 1, wherein at least one of the front and rear slits has a profile of non-uniform width in a direction transverse to the beam plane.

14. The apparatus according to claim 1, wherein the front and rear slits have a dimension transverse to the beam axis that is no greater than 50 μm.

15. The apparatus according to claim 14, wherein the dimension of the slits is no greater than 10 μm.

16. A method for analysis of a sample, comprising: directing a beam of radiation along a beam axis to impinge on a target area on a surface of the sample; interposing in the beam a beam blocker containing front and rear slits that together define a beam plane that contains the beam axis and passes through the target area, so that a lower side of the beam blocker adjoins the surface of the sample and so that the beam of radiation passes through the front slit before impinging on the target area, and the radiation scattered from the sample within the beam plane passes through the rear slit; and sensing the radiation scattered from the sample after passage of the radiation through the rear slit.

17. The method according to claim 16, wherein the beam is directed so that the radiation converges on the target area over a range of elevation angles relative to the surface of the sample, and wherein sensing the radiation comprises resolving the scattered radiation as a function of elevation angle.

18. The method according to claim 17, wherein the radiation comprises X-rays, and wherein resolving the scattered radiation comprises detecting a reflectometric spectrum of the X-rays, which is indicative of a characteristic of a thin film on the surface of the sample in the target area.

19. The method according to claim 16, wherein the beam blocker has a width between the front and rear slits, and wherein interposing the beam blocker comprises positioning the beam blocker so that the lower side is separated from the surface of the sample by a gap of a given height, and choosing the width and height so as to block the radiation that is emitted from the radiation source at elevation angles greater than a given angle relative to the surface of the sample from passing through the gap.

20. The method according to claim 19, wherein the width and height are chosen so as to satisfy a relation $\alpha_{min} \cong 2\,h/W$, wherein $\alpha_{min}$ is the given angle, h is the height, and W is the width.

21. The method according to claim 20, wherein directing the beam comprises positioning a shutter between a source of the radiation and the sample so as to block the radiation that is emitted from the source below the given angle.

22. The method according to claim 16, and comprising positioning a beam limiter, comprising a knife edge, between the front and rear slits transverse to the beam plane, such that the knife edge protrudes between the lower side of the beam blocker parallel to the surface of the sample and adjacent to the target area so as to define a gap between the surface and the knife edge and to block a portion of the beam that does not pass through the gap.

23. The method according to claim 22, wherein a lower side of the knife edge, adjacent to the target area, is rounded.

24. The method according to claim 22, wherein the gap is no greater than 3 μm.

25. The method according to claim 16, wherein the front and rear slits have a dimension transverse to the beam axis that is no greater than 50 μm.

26. The method according to claim 25, wherein the dimension of the slits is no greater than 10 μm.

* * * * *